US008080406B2

(12) United States Patent
Gaalswyk

(10) Patent No.: US 8,080,406 B2
(45) Date of Patent: Dec. 20, 2011

(54) ETHANOL PRODUCTION SYSTEM

(76) Inventor: Mark K. Gaalswyk, Welcome, MN (US)

(*) Notice: Subject to any disclaimer, the term of this patent is extended or adjusted under 35 U.S.C. 154(b) by 1094 days.

(21) Appl. No.: 11/131,854

(22) Filed: May 18, 2005

(65) Prior Publication Data

US 2005/0260554 A1 Nov. 24, 2005

Related U.S. Application Data

(60) Provisional application No. 60/574,300, filed on May 24, 2004.

(51) Int. Cl.
*C12M 1/36* (2006.01)
*C12M 1/38* (2006.01)
*C12M 3/00* (2006.01)

(52) U.S. Cl. ...... 435/286.5; 435/3; 435/161; 435/286.1; 435/289.1

(58) Field of Classification Search .............. 435/286.5; 203/19, 100; 426/11, 30
See application file for complete search history.

(56) References Cited

U.S. PATENT DOCUMENTS

| | | | | |
|---|---|---|---|---|
| 3,410,765 A | * | 11/1968 | Bodine | 203/10 |
| 4,494,451 A | * | 1/1985 | Hickey | 99/276 |
| 4,652,451 A | * | 3/1987 | Leedham et al. | 426/11 |
| 4,654,215 A | * | 3/1987 | Yamada et al. | 426/17 |
| 5,196,069 A | * | 3/1993 | Cullingford et al. | 127/37 |
| 5,545,543 A | * | 8/1996 | Zinnamosca et al. | 435/162 |
| 5,559,031 A | * | 9/1996 | Zinnamosca et al. | 435/289.1 |
| 5,962,054 A | * | 10/1999 | Kozempel et al. | 426/241 |
| 2002/0122850 A1 | * | 9/2002 | Kartchner | 426/241 |

OTHER PUBLICATIONS

US Department of Energy, "Fuel From Farms: A Guide to Small-Scale Ethanol Production", Feb. 1980, Technical Information Center US Department of Energy, Specifically pp. 31-70.*
Westby, Carl; Gibbons, William, "Farm-Scale Production of Fuel Ethanol and Wet Grain from Corn in a Batch Process", 1982, Biotechnology and Bioengineering, vol. XXIV, pp. 1681-1699.*
Askin, Stephen, "Advanced Brewhouse Operation Utilizing High Level Cell Control", Oct. 1988, Programmable Control and Automation Technology Conference and Exhibition,1988 Conference Proceedings. Fourth Annual Canadian, pp. 13A1-5/1-2.*
Qiang, Sheng, "PLC-based Control Systems for Industrial Production of Fuel Alcohol", Dec. 2002, Industrial Technology, IEEE International Conference, vol. 2, pp. 827-832.*
US Department of Energy, "Fuel From Farms: A Guide to Small-Scale Ethanol Production", Feb. 1980, Technical Information Center US Department of Energy, Specifically pp. 31-70.*
Askin, Stephen, "Advanced Brewhouse Operation Utilizing High Level Cell Control", Oct. 1988, Programmable Control and Automation Technology Conference and Exhibition, 1988 Conference Proceedings. Fourth Annual Canadian, pp. 13A1-5/1-2.*
Askin, S.; , "Advanced brewhouse operation utilizing high level cell control," Programmable Control and Automation Technology Conference and Exhibition, 1988. Conference Proceedings., Fourth Annual Canadian , vol., no., pp. 13A1-5/1-2, Oct. 12-13, 1988 doi: 10.1109/PROCCE.1988.82240 (Including citation page attached to NPL).*

* cited by examiner

*Primary Examiner* — William H Beisner
*Assistant Examiner* — Danielle Henkel
(74) *Attorney, Agent, or Firm* — Sturm & Fix LLP

(57) ABSTRACT

The present invention provides a method of automating the production of ethanol in an economical method yet maximizing the conversion of grains into ethanol in an even greater conversion efficiency with a greatly improved feed value byproduct.

17 Claims, 14 Drawing Sheets

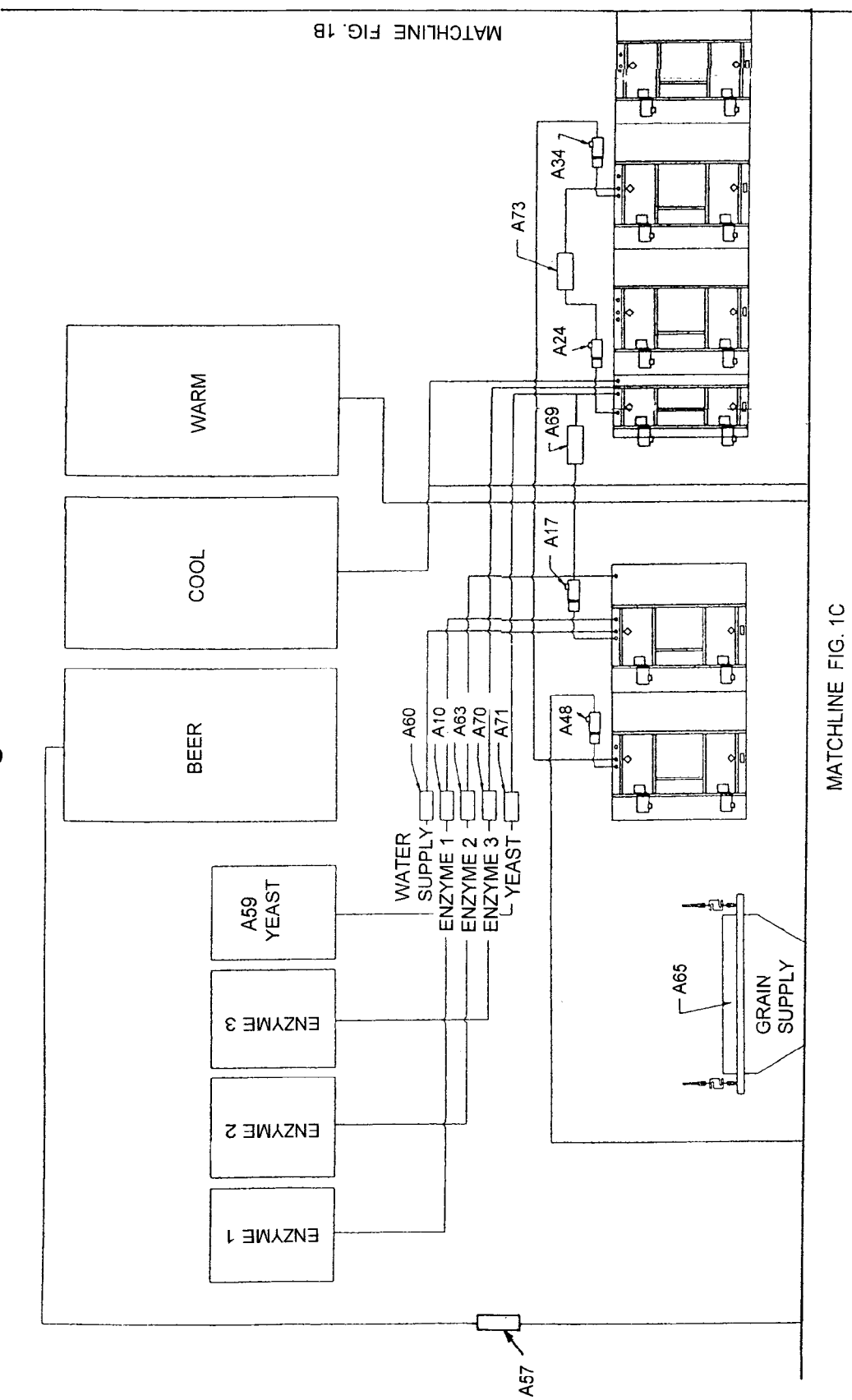

ROW DISTRIBUTION PANEL

MODULE STARTER PANEL

MODULE CONTROL PANEL - INSIDE DOOR

GRAIN CONTROL M.S.P. #4

MODULE CONTROL PANEL - BACKPLATE

ETHANOL PRODUCTION SYSTEM

CROSS REFERENCE TO RELATED APPLICATIONS

This application claims the benefit of U.S. Provisional Patent Application Ser. No. 60/574,300 filed May 24, 2004 entitled "Ethanol Production System."

BACKGROUND OF THE INVENTION

1. Field of the Invention

The present invention relates to the field of chemical processing, and more particularly to a method for the efficient production of ethanol.

2. Description of Related Art

The prior art is replete with myriad and diverse methods of producing ethanol.

The conventional commercial method of creating ethanol consists of using a number of very large (10 thousand gallon plus) tanks. The historical reason for using the large tank method is that the method of automating such a system was more economical. The drawback was that the conversion process of converting grain into ethanol was less efficient in very large batch quantities versus using a series of smaller tanks that allow greater agitation of the product and more uniform distribution of fermentation activation agents. In the past, making ethanol from a series of small tanks required a very high manual labor component that made large scale, 24 hour per day production very expensive and not economically feasible.

While prior art methods of producing ethanol are adequate for the basic purpose and function for which they have been specifically designed, they are uniformly deficient with respect to their failure to provide a simple, efficient, and practical method of automating the production of ethanol.

As a consequence of the foregoing situation, there has existed a longstanding need for a new and improved method of producing ethanol, and the provision of such a method is a stated objective of the present invention.

BRIEF SUMMARY OF THE INVENTION

Briefly stated, the present invention provides a method of automating the production of ethanol in an economical method yet maximizing the conversion of grains into ethanol in an even greater conversion efficiency with a greatly improved feed value byproduct.

This method enables ethanol to be produced for about 55 cents per gallon, versus the more normal $1 per gallon of the other existing methods. The feed byproduct is also worth about twice as much because the lower temperatures allow for much of the fat to be left in the feed.

Another positive is that the system does not require an EPA permit because no dangerous pollution is released to the atmosphere. The system can be set in virtually any existing building, with the plan of turning every grain storage, machine shed, and unused old factory into an ethanol plant. Finally, as the system is scaleable, up to just one unit can be made up for a farmer to convert his own crop, or place, say 64 of them in a facility and make a 50 million gallon per year plant.

An object of the present invention is to provide an economically feasible process where the feed nutrient quality of the feed byproduct has much greater feed value.

Another object of this is to allow for an economically feasible operation of the small tank method that can also be used as a research vehicle to test different varieties and types of grains and ethanol production processes individually without requiring a change over of the entire plant, since each and every batch of ethanol can be produced according to its own specified ethanol batch parameters.

Yet another object of this invention is to allow the economical and efficient automatic production of ethanol in a more efficient small tank method.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figures 1, 1A, 1B, 1C, 1D:
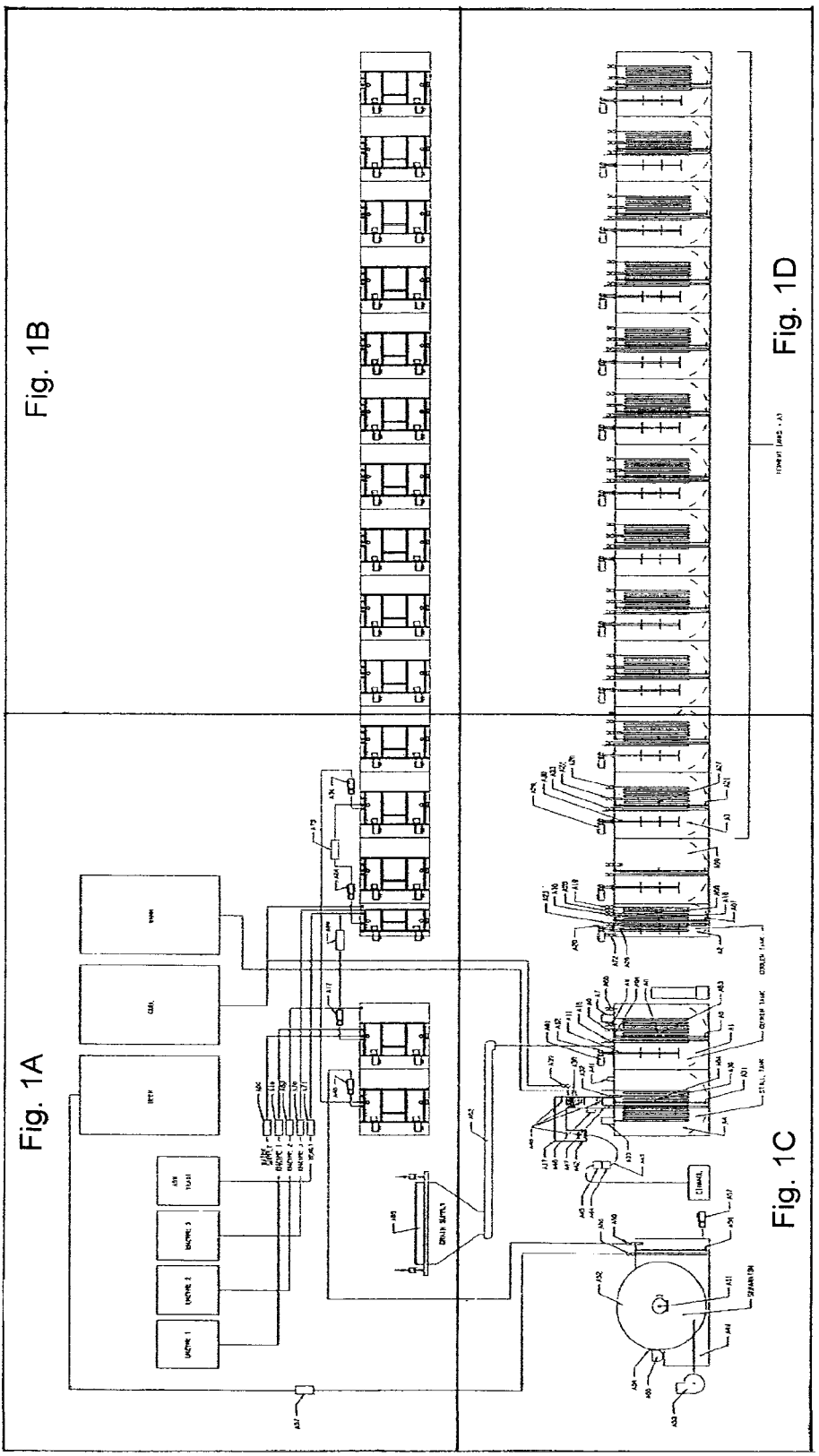
FIG. 1 is a schematic representation showing the process equipment used in practicing the method of the present invention.
FIG. 1A is an enlarged schematic representation corresponding to the upper right quadrant of FIG. 1.
FIG. 1B is an enlarged schematic representation corresponding to the upper left quadrant of FIG. 1.
FIG. 1C is an enlarged schematic representation corresponding to the lower right quadrant of FIG. 1.
FIG. 1D is an enlarged schematic representation corresponding to the lower left quadrant of FIG. 1.
Figure 1B:
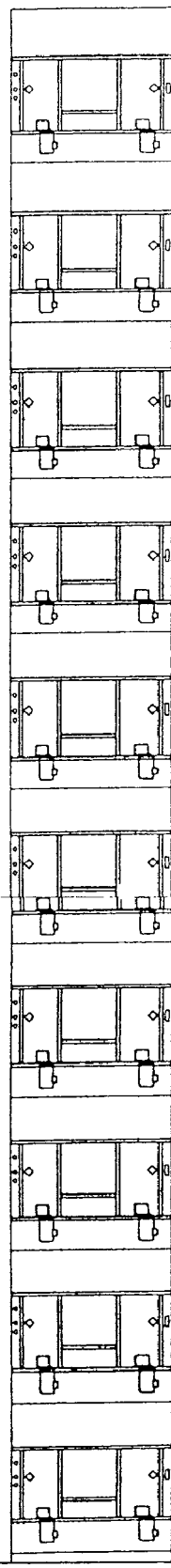
Figure 1C:
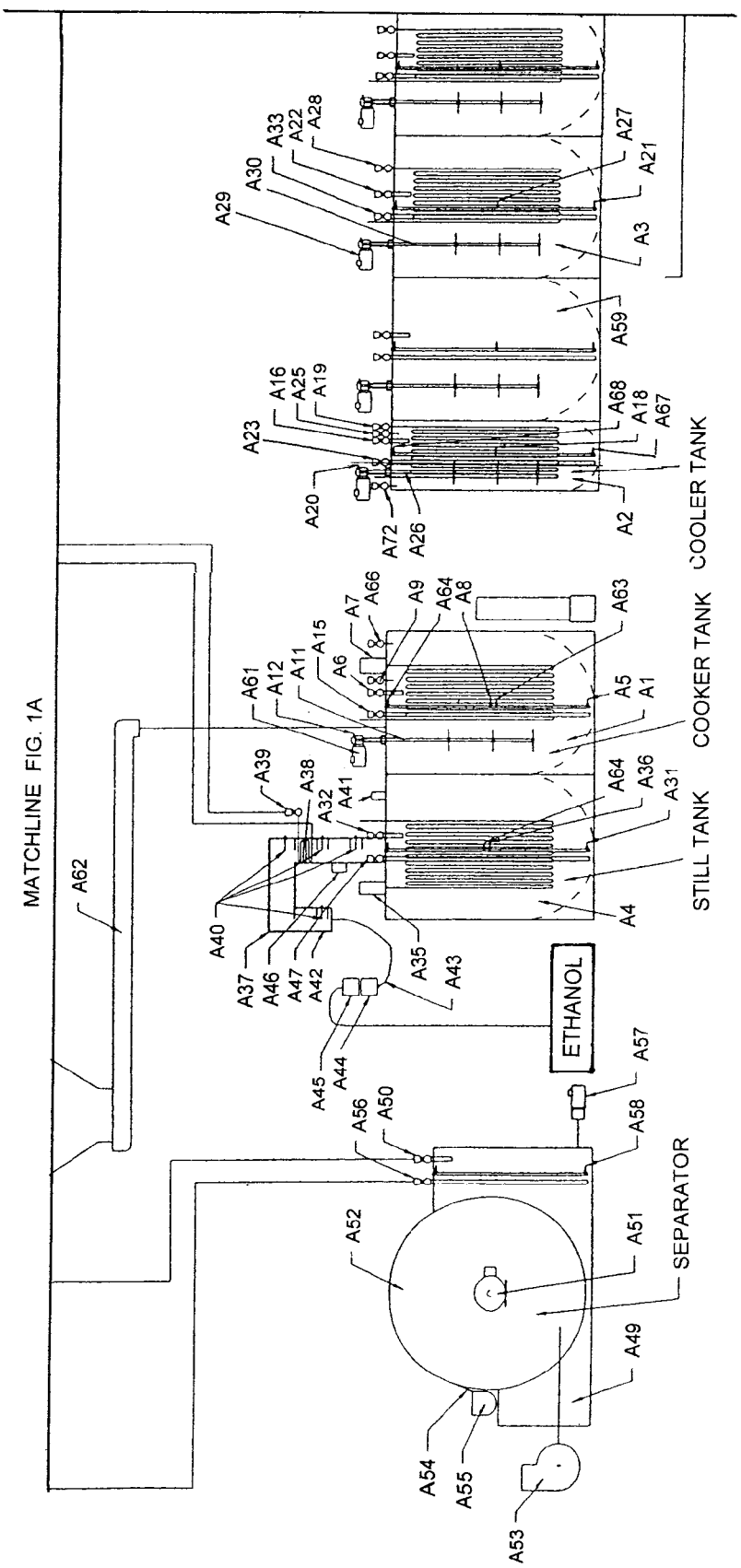
Figure 1D:
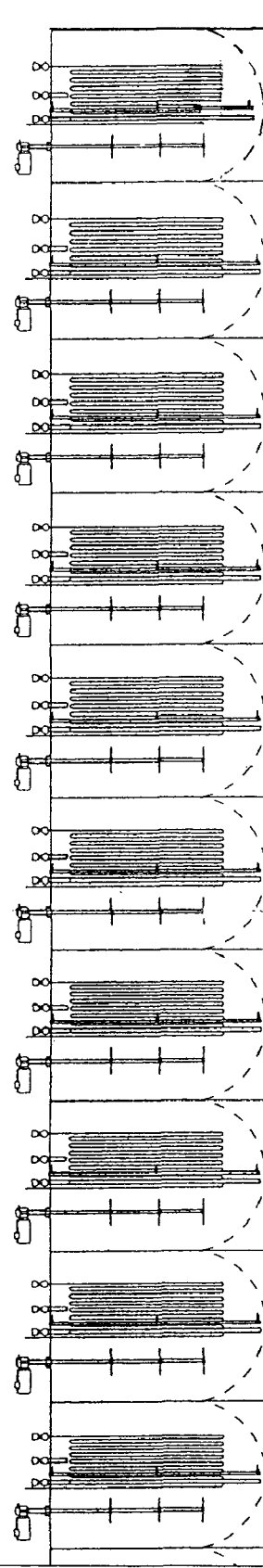
Figure 2A:
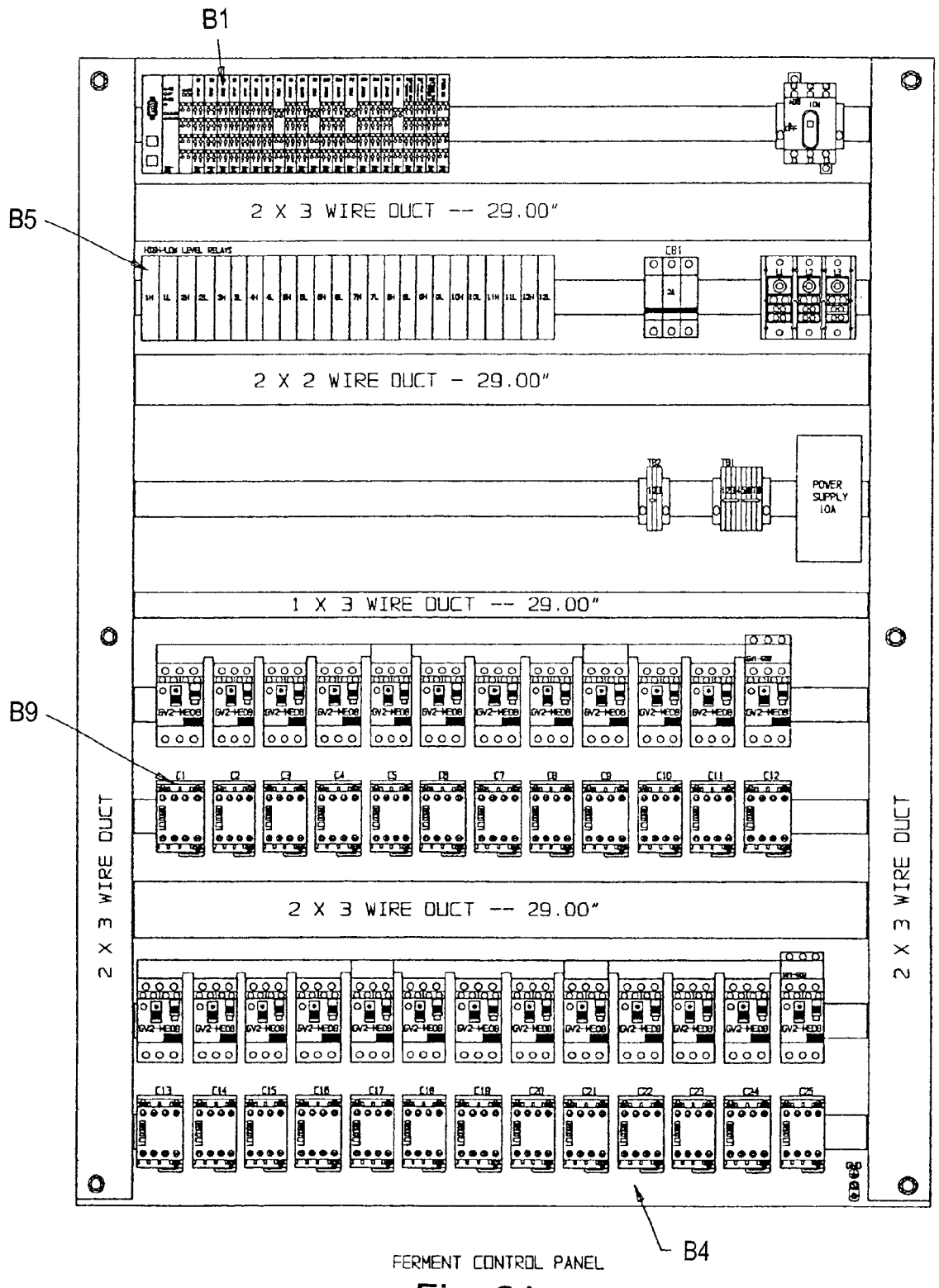
FIG. 2A is a front elevational view of the ferment control panel.
Figure 2B:
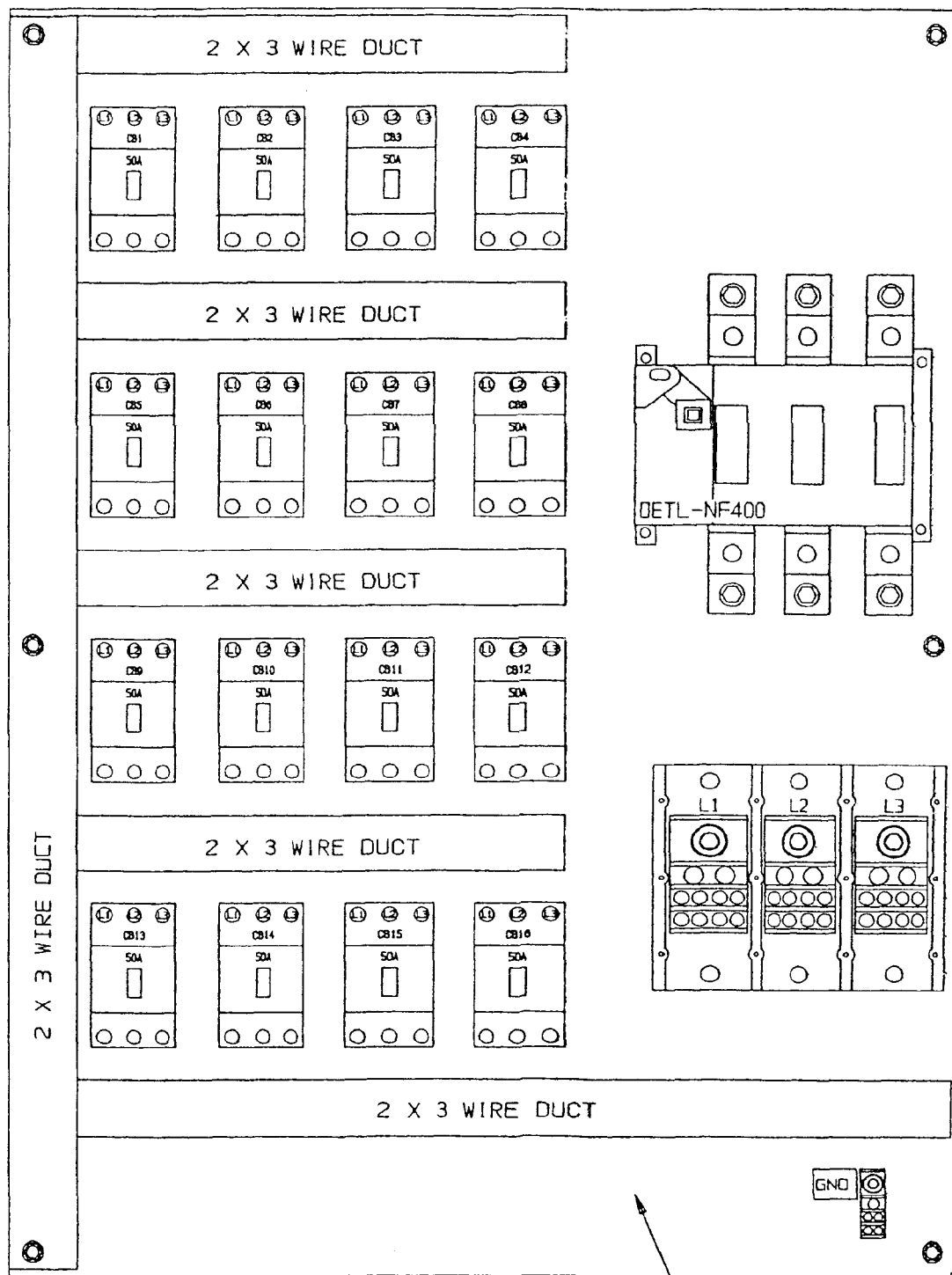
FIG. 2B is a front elevational view of the row distribution panel.
Figure 2C:
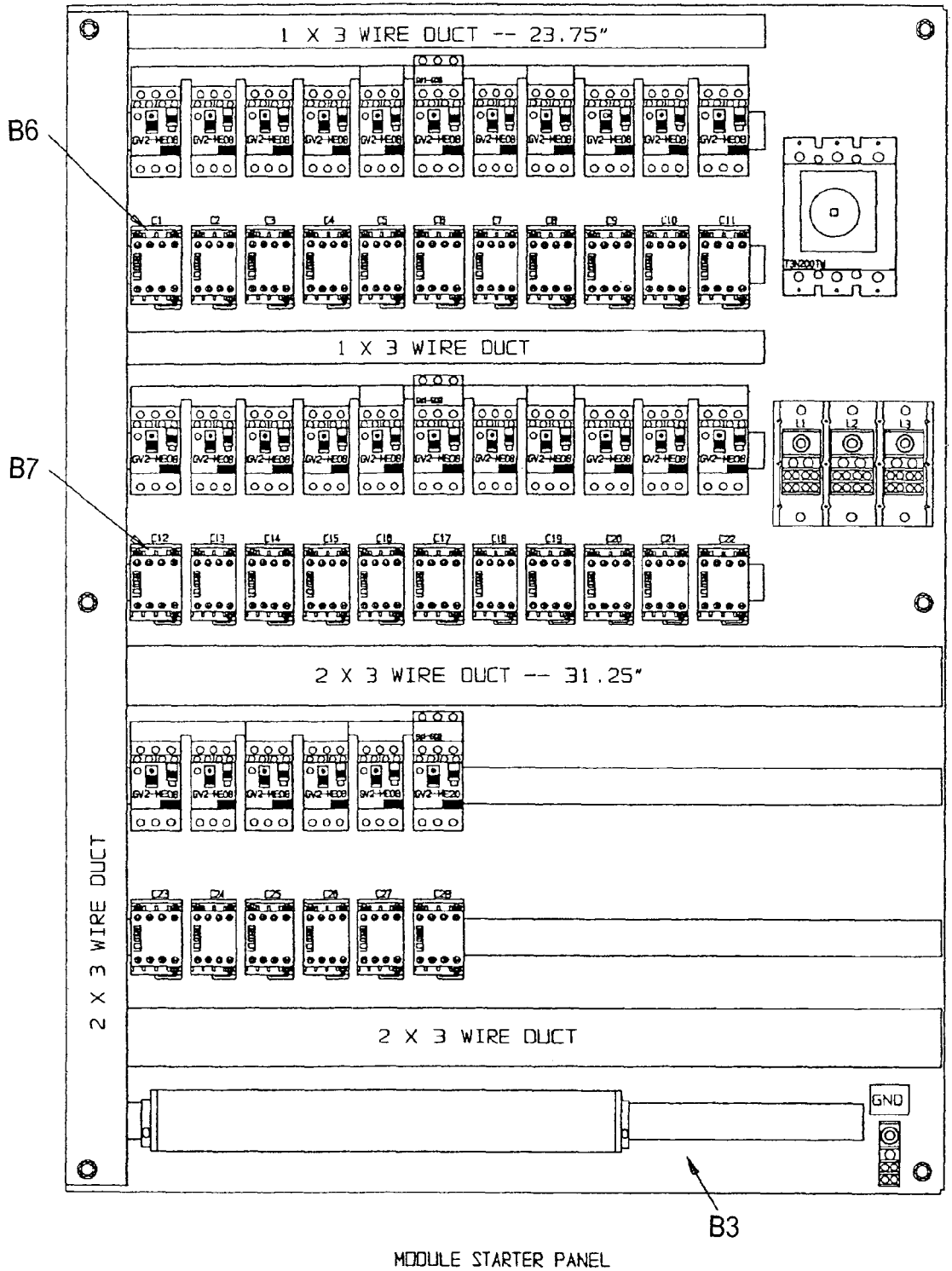
FIG. 2C is a front elevational view of the modular starter panel.
Figure 2D:
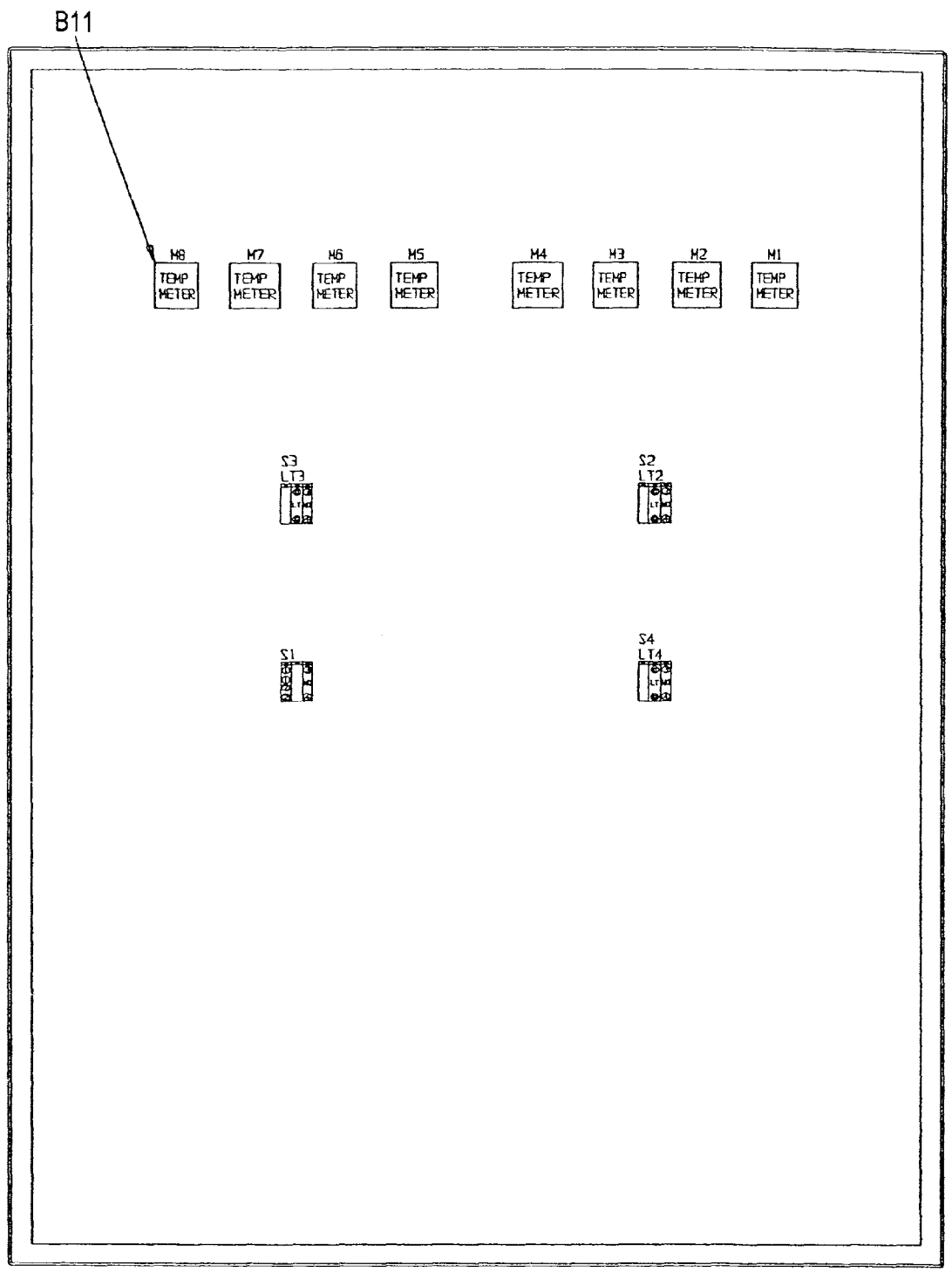
FIG. 2D is a front elevational view of the modular control panel, inside door.
Figure 2E:
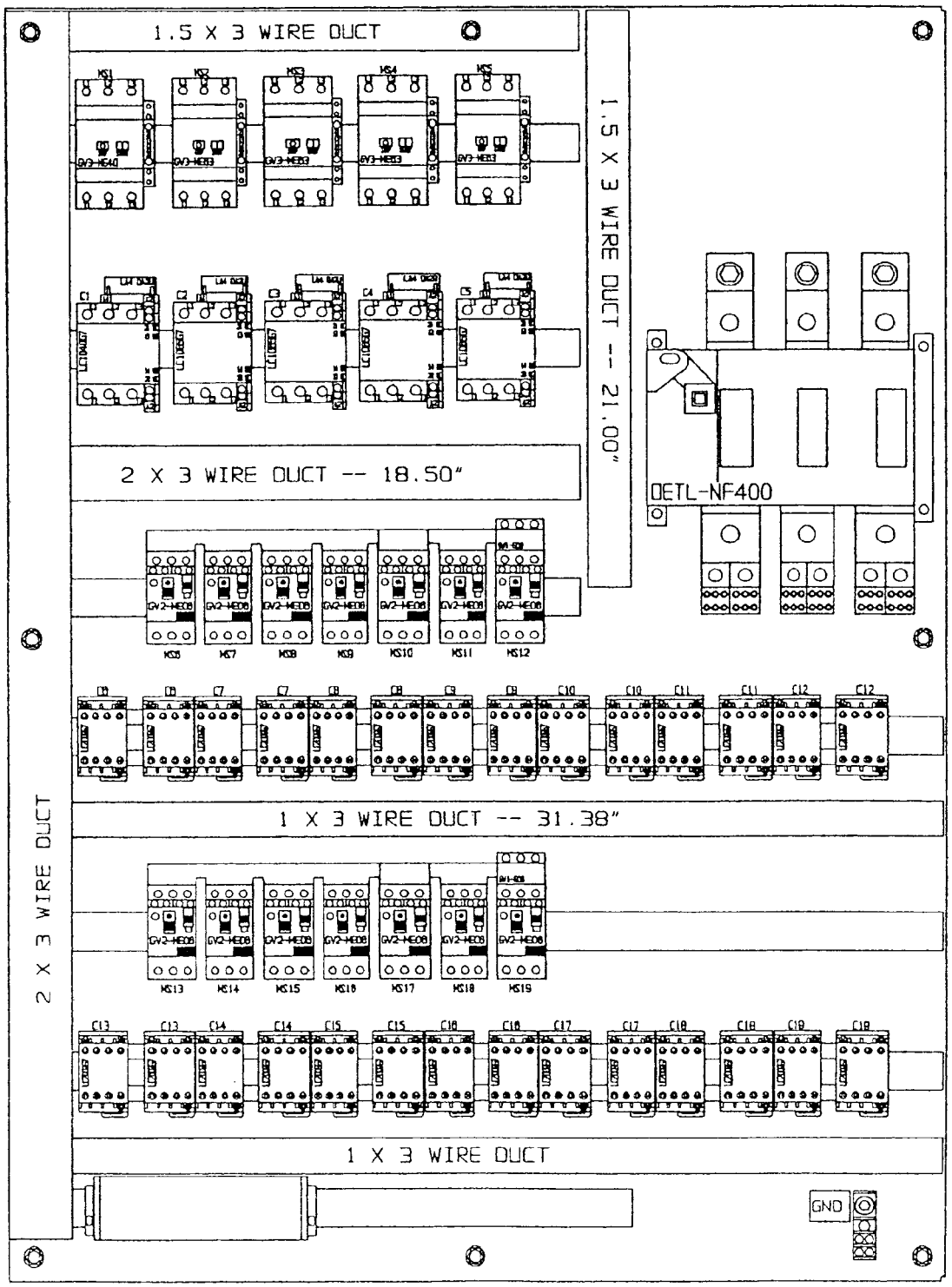
FIG. 2E is a front elevational view of the grain control M.S.P. #1 and #2.
Figure 2F:
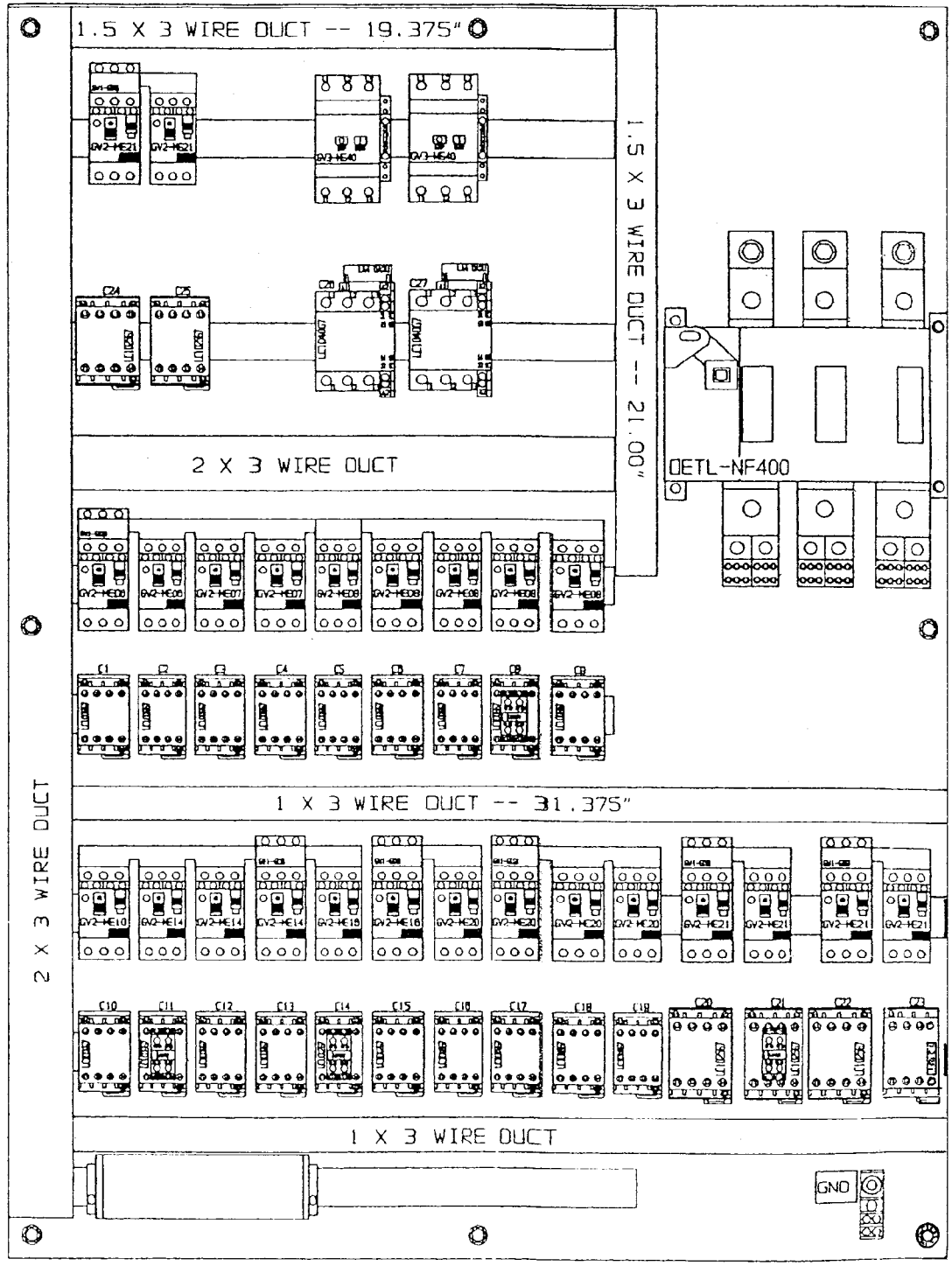
FIG. 2F is a front elevational view of the grain control M.S.P. #3.
Figure 2G:
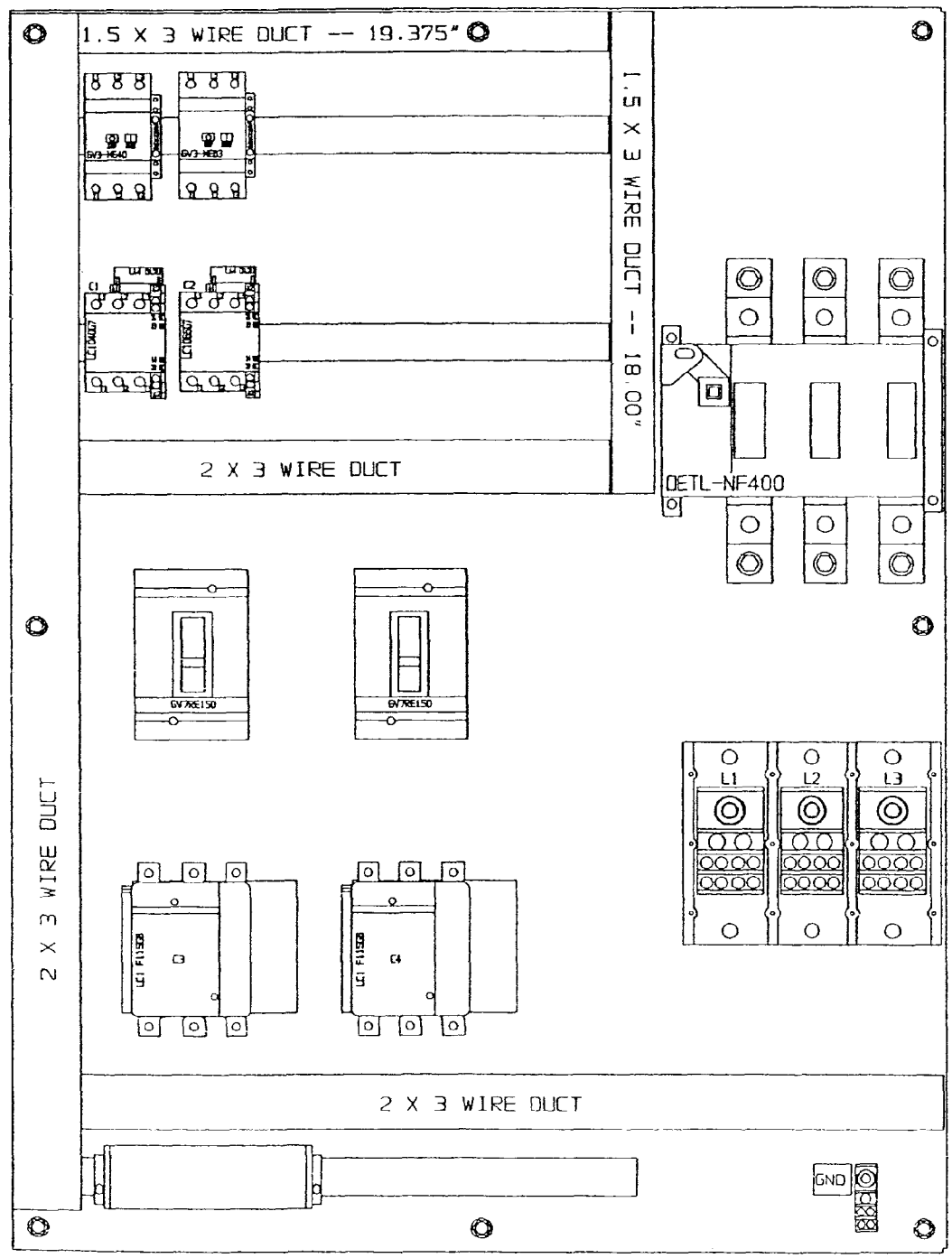
FIG. 2G is a front elevational view of the grain control M.S.P. #4.
Figure 2H:
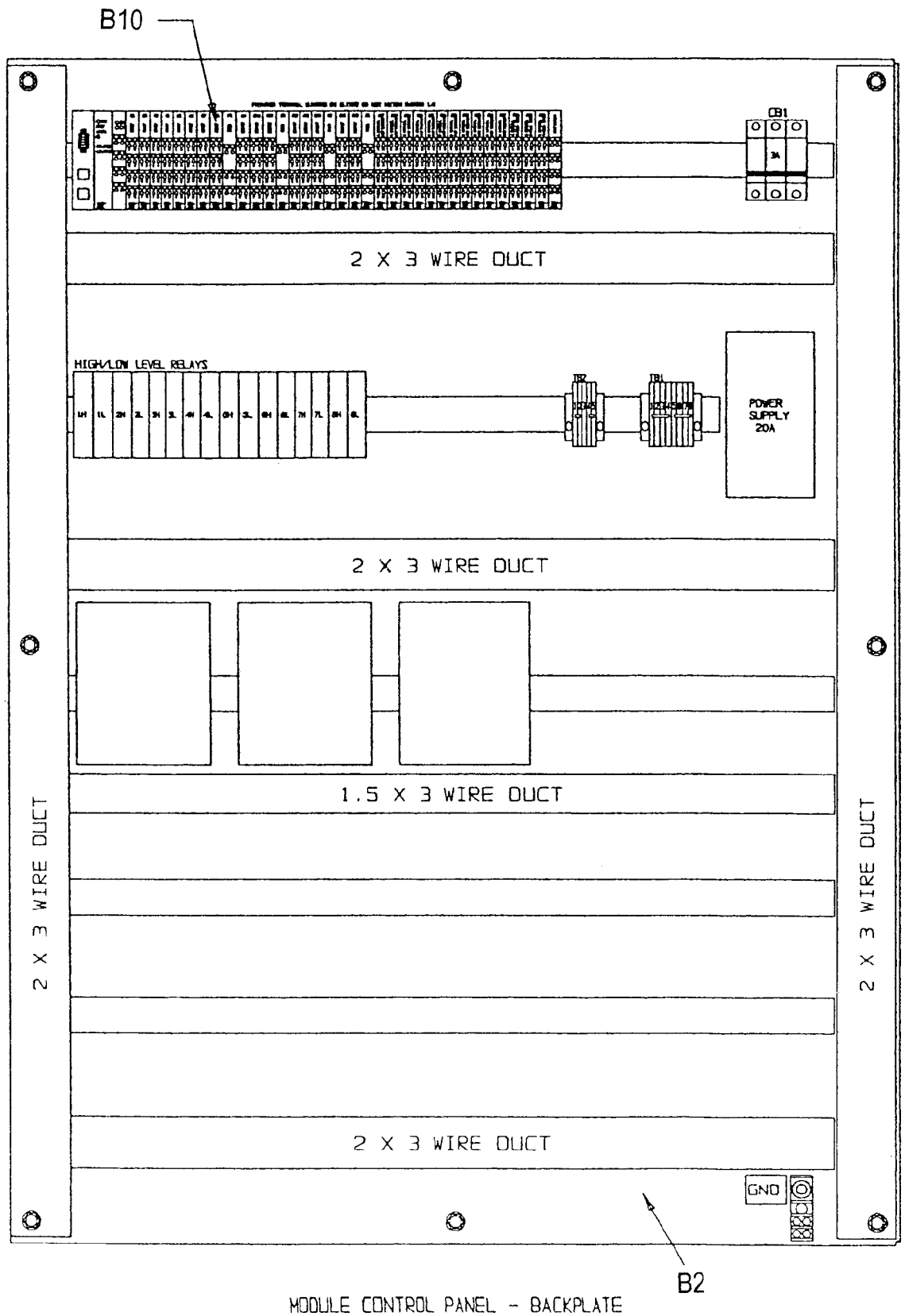
FIG. 2H is a front elevational view of the modular control panel, backplate.
Figure 3:
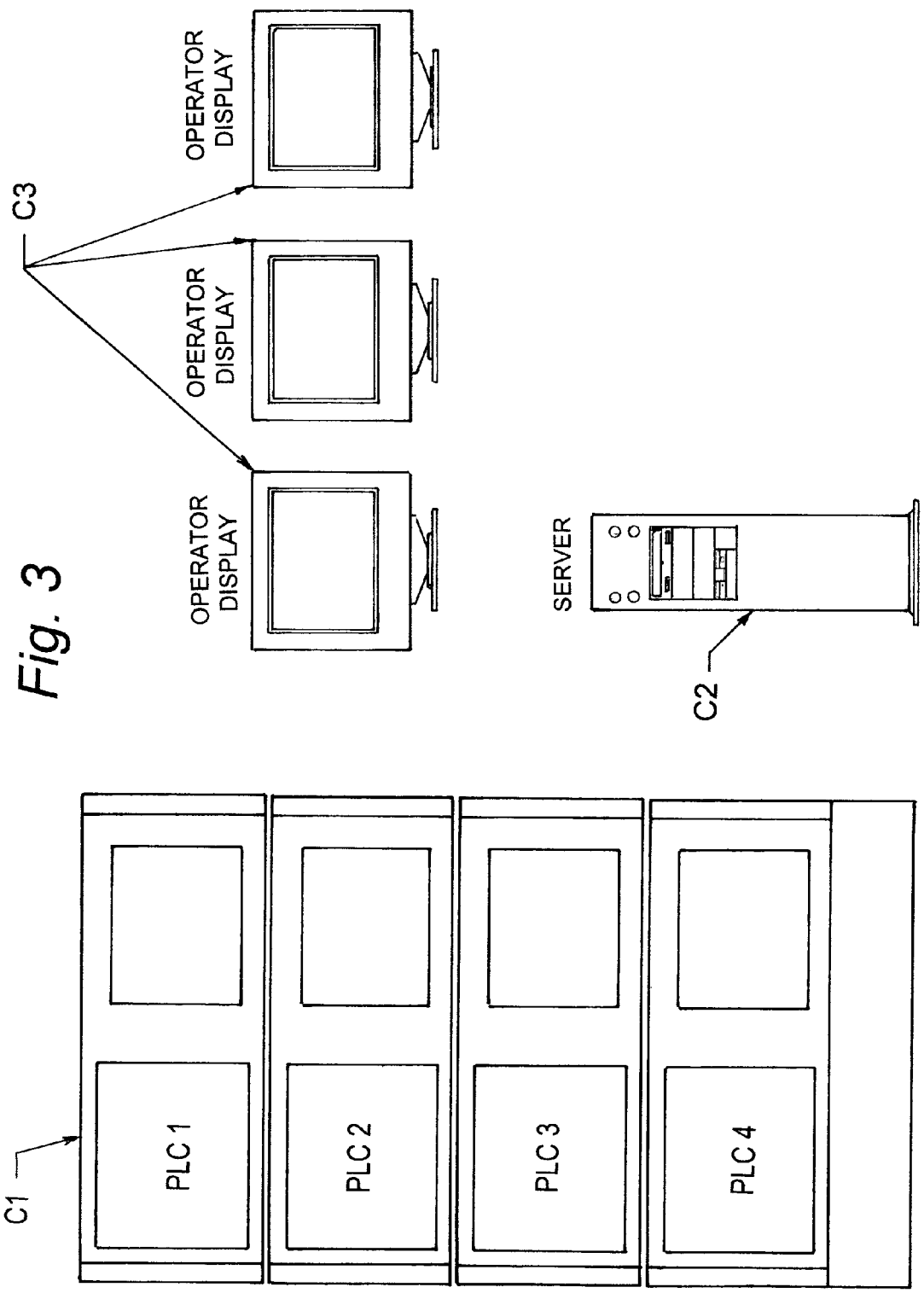
FIG. 3 is a schematic representation of the process control hardware.

As can be seen by reference to the drawings, and in particular to FIG. 1, the processing equipment used to practice the method of the present invention is schematically represented.

The system consists of a primary PLC (C1) (could also be a PC) logic controller that is—hereafter referred to as PLC or PLC system connected to hundreds of distributed I/O points. Although other brands of equipment could also be used, for this particular implementation of the invention we utilized a soft PLC-PLC and a WAGO type distributed I/O using a profy bus communications network (see FIG. B1). A control box (B2) was located next to each of four cookers, four stills and one cooling tank to automate all of the functions required for these tanks. Another control box (B4) was located next to the fermentation tanks to operate the functions contained within. The invention as described does not depend on how the control panels were chosen to be located. Although not a numerical requirement, the implementation of this invention utilized 12 fermentation tanks (A3) to allow for sufficient tanks to allow a near continuous flow of cooking and stilling, as the fermentation cycle of the process takes much longer than the still and cooking cycles.

Each of the distributed nodes contain input output slices (B10). Each slice can handle different functions such as digital inputs, digital outputs, 4-20 ma inputs, temperature inputs, load cell inputs, analog inputs and analog outputs. At each node, we located the slices of I/O required to operate the functions performed in this general vicinity.

The system consists of a series of small tanks. The tanks can be identical, except one of the tanks can have components lowered into them to allow that tank to form as a cooker (A1). Another can be used as a cooling tank (A2). Another set of tanks can be used a fermentation tanks (A3). Another tank can be used as the still (A4). Although not fixed, the system illustrated consists of 12 fermentation tanks for each one cooker tank, one still tank, and one cooler tank. The system could also be configured with yet an optional yeast tank (A59).

The process begins by the PLC (C1) recalling from the memory, hard drive or other data storage means the specifications and parameters for making the particular batch of ethanol. These specifications among other things will contain the prescribed amount and mixture of: grain, water, enzymes, yeast and ethanol cooking, fermenting time, distilling conversion time, temperature with time intervals, volumes of agents, and weight parameters.

Cooking Phase

The PLC will look at the sensor located in the bottom of the cooker tank (A5) to verify that the tank is indeed empty. This step may be skipped if previous logic and through its process already emptied the tank of material. The sensor may be any type of liquid/mash level detection. The type used in the example was a small nylon adaptor with an internal rod. This rod would provide conductivity of a small electrical current that will be conducted from the rod through the material and picked up by the outer sides of the tank directly and then sent back to a liquid level module (B5) Although not a requirement, the brand of liquid level module used in this invention was a Turck brand.

Once the PLC determines that the tank is empty, it will then activate a voltage output through the network node (B10) that will then activate an air solenoid valve. This air solenoid valve will then actuate a water solenoid valve (A6) that is plumbed to the particular cooker tank currently needing to be filled with water. The actuation of the valve will allow the already pressurized water to begin flowing through the valve and into the cooker tank (A1). The actual valves used may be either air or electric depending on costs—although an air operated valve will typically be less costly and provide for longer operational life. The water flowing through the valve will also flow through a volume liquid meter. (A60). The PLC (C1) will look at the gallons flowing through the liquid meter and compare this with the amount contained within the previously retrieved batch parameters detailing amount of water to begin the batch with. Once the desired amount of water has flowed through the valve and entered the cooker, the PLC will turn off the output and allow the valve (A6) to turn off and water flow to discontinue into the cooker tank.

The system will then meter in the correct amount of grain as specified in the batch parameters. This amount of grain could either be weighed as part of the control process, or weighed or metered in volumetrically ahead of time in a container (A65) ready to be transferred into the cooker. The PLC will activate an output through the distributive I/O and activate the auger or conveyor connected to the grain supply (A62) apparatus as required to convey the grain material into the cooker.

The PLC will then turn on some type of heating device (A3) to heat up the mixture of grain and water to the needed cooking temperature. This device may be either a conventional gas fired burner with coils located within the tank to distribute the heat or a more modern micro wave type device. Regardless of the method, the mixture will be brought up to the desired temperature as recalled from the batch parameters. The temperature of the slurry of material is observed through a cooker temperature probe (A8.)

This probe as used in the invention was a RTD type temperature probe although other types of temperature diction probes can also be utilized such as a thermocouple or other. This temperature level is then fed into the PLC distributed network via a temperature monitoring slice module connected to the I/O network. (B10) This module then conveys the observed temperature through the I/O network back to the PLC where the observed temperature is compared with the retrieved batch parameters to determine if the burner (A7) or micro wave device should continue to warm up the material contained within the cooker.

As an added level of safety but not a requirement, the system optionally provides for a separate temperature monitoring meter (B11). There is one of these for each tank containing a heating unit. It is connected to its own separate temperature probe—(A63) in the cooker and (A64) in the still. The outputs to activate the heat source for each of the respective tanks is wired through the contacts contained within each of these respective meters. This redundancy provides an added element of safety so should a primary temperature probe or module fail, the high level limits set in this meter will activate and shut off the burner preventing an over temperature event from occurring. This meter is also wired into the distributed I/O node as a secondary feed of temperatures values into the PLC to provide for the software to compare temperatures to make certain they are within an acceptable tolerance of each other for further temperature validation.

Before, after, or during the heating process, the PLC will also turn on a valve (A9)—look at enzyme volume meter (A10) and include the required amount of enzyme into the mixture. One type of such enzyme is proteaze although technology will improve and allow other various enzymes to be used. The enzyme being utilized in the present invention was in a liquid form, although a dry form could also be utilized by then metering in volumetrically or weighing in the correct amount of enzyme.

At some point during the heating process, the PLC control will then turn on one or more agitators (A11) located within the cooker tank. These agitators will be activated by having the PLC provide a voltage to a motor contactor (B6) that then allows the voltage to flow from the electrical supply (in this case electrical distribution box (B8) through the main disconnect of module starter panel box (B3) and through contactor (B6) to the agitator motors (A61) located on the tank. Once the motors are activated, the PLC will verify the rotation of the agitator shafts by the means of a shaft rotation verification device such as an inductive proximity sensor (A12) mounted close to the rotating shaft with a protruding metal bump that provides a sensing indication when the bump on the shaft is in close proximity to the sensor. This input is then fed back to the PLC and either the remote node (B10) or the PLC can then observe the sensor indication verifying agitator shaft rotation. An alternative method could include other various shaft rotation monitoring devices. For this example, the actual logic coding was placed to read the inductive proximity sensor for shaft rotation into the small amount of processing available in the small logic PLC located within the network node itself (B10). This logic will then only need to transmit through the network an indicator of shaft rotation present or not present and avoid placing the very large amount of shaft rotation processing on the distributive network and slowing down the overall network data collection and operation.

The heating device burner or microwave (A7) is continued to be activated while the mixture of grain, water, and enzyme is being heated. The temperature is again raised up to the even warmer cooking temperature as observed by cooker temperature probe. (A8) The process is similar to the temperature observing and material warming process described above.

The temperature of the slurry material along with the agitation continuation is maintained for a described time interval as retrieved from the batch parameters. The PLC does this by comparing a timer value with the cook time duration parameter retrieved as specified for this current batch.

Once the material has been cooked and agitated at the desired temperature for the defined time period, the system may either add optionally additional enzymes through volume meter (A63) similar to the previous addition of enzyme or just complete the cooking process. The addition of enzyme or other materials, cooking, agitating for desired time interval and cooking at desired temperature for defined time period will be repeated for as many times as defined within the batch parameters retrieved. For this invention example, a second enzyme (alpha ameleaize) was added to the batch.

This cycle will continue until the batch material is ready for the cooling phase.

Cooling Phase

Once all of the additions of agents and cooking and agitating for desired time intervals have been achieved, the system will then enter the cooling phase of the process. This is achieved as described in this invention by the use of a cooling tank (A2) or may optionally be skipped with cooling occurring in the cooker tank itself or else in one of the selected fermentation tanks (A3).

If the cooling tank is used, the PLC will observe the liquid level sensor (A67) in the cooling tank to make sure tank is empty in a manner similar to the aforementioned liquid level detection described in the cooker. If the tank is empty, the PLC will then activate the cooker empty solenoid valve (A15) and the cooler tank fill valve (A16) in a manner similar to the liquid valve activation described above. The PLC will then activate the cooker empty pump (A17) and pump the slurry from the cooker through the cooker empty solenoid valve (A15) through the cooling tank fill solenoid valve (A16) and into the cooling tank. While this pumping is continuing, the PLC system will optionally compare a cooker tank empty max time parameter stored with the batch and the actual time occurring for the pumping of the slurry from the cooker into the cooling tank. As a further safety precaution, the system will optionally look at the cooling high level liquid level sensor (A68) and make sure that the tank is not overfilled. It will check this high level in a manner similar to that used to verify that the cooking tank was not over filled. If either the maximum time value is exceeded or the high liquid level safety sensor is tripped, the PLC system will indicate an error and discontinue the pumping of the liquid. As an even further verification that the material is indeed pumping, the PLC system will have optionally observed during the pumping process that the cooling temperature probe (A18) will have detected a change in temperature midway through the filling process. All of the various time, liquid sensing and temperature sensing observed during the pumping process is optional and is only included to better ensure that nothing wrong is taking place during the tank filling process such as a solenoid valve not functioning, a broken pipe, a plugged pipe etc. Still another, yet optional method may include mounting a sensor on the various solenoid valves with feed back to determine their actual position or flow meter presence within the lines.

The PLC system will continue pumping the material from the cooker into the cooling tank until the low liquid level sensor in the cooker (A5) no longer detects the presence of the slurry or the max time has expired. If this occurs, the system will generate an error condition for the operator. Once the low level is detected, the system will continue to pump for an additional pump and line clean out time period as retrieved from the batch parameters. Once the clean out time has expired, the PLC system will then deactivate the pump (A17) and close the opened solenoids to complete clean out. Optionally, the system could include a small line purge routine to run a small amount of clean water through the line and into the cooling tank to purge the line. To prevent harmful bacteria from remaining in the pipe, a micro wave signal (A69) is passed through the material flowing to the cooling tank to kill the bad bacteria.

Once the material from the cooker is all into the cooling tank, the PLC will repeat the cooking process described above with another batch of material. Before repeating, an added but not necessarily needed capability of the system is that the PLC system will look at the various processes occurring in the available tanks and determine that if it completes another cooker batch in the time parameters as defined by retrieved cooking parameters—that a ferment tank or cooling tank will be available to convey the material to. If not, the system will delay starting another batch until is has determined it will be able to finish and go somewhere with the material when done cooking the next batch.

Meanwhile, the PLC system (C1) will begin cooling the slurry in the cooling tank by activating the cooling tank heat exchange solenoid (A19) and allowing cool water to flow through the valve and through the cooling heat exchange tubes protruding into the slurry. This action will then begin to cool the material. The PLC will continue to cool the material in the cooling tank by observing the cooling tank temperature probe (A18) and comparing it with the parameters retrieved for the batch. Once the material has reached the desired temperature the PLC will also include yeast or other fermentation activation materials into the mixture. This yeast may be included by activating a valve (A25) and metering in volumetrically, either as liquid or dry yeast, material through meter (A71). The amount of yeast material included will have also been stored in the retrieved batch parameters with the PLC comparing the amount included into the mixture with the amount defined in the retrieved parameters. If the yeast is added in a liquid format, the system could use this from an optional yeast tank (A59). If this was used, the tank can either contain the liquid yeast or the system will measure in by either weight or volumetrically the correct amount of dry yeast into a water slurry. Agitate the mixture and then provide a supply of active liquid yeast as needed for the system. Similarly, the system will add additional activation agents and enzymes as need (in this case glucoameleaize) by activating the additional enzyme valve (A72) and observing flow of liquid enzyme through volume meter (A70)

The entire time the cooling is taking place, the PLC system would have activated cooling agitators (A26) by turning on the motors connected to such by activating cooling motor starter contactors (B7) by outputting through the distributed I/O network slice (B10) the voltage required to turn on these agitators. Again, once the agitators were turned on by the PLC, the system would verify their rotation similar to the method described above regarding the cooker tank agitator rotation verification by looking at the inductive proximity sensor (A20).

The process of cooling to a prescribed temperature, agitating for a batch parameter defined time period, and metering in a defined amount of yeast or activating ingredient is repeated over and over for each repeated activation ingredient until all required ingredients have been added, desired temperatures have been reached, and the time period described for each has elapsed. Once this is all completed, the cooling phase has been completed and the material is ready to go into the fermentation stage.

Fermentation Stage

Once the cooling stage has been completed—either in a separate cooling tank, the original cooker, or in the fermentation tank—the material is then ready to enter the fermentation stage.

One or optionally many fermentation tanks may be used. In this example, 12 fermentation tanks were utilized as this provided for a more continuous cooking and stilling process, due to the fact that the fermentation cycle time duration (about 38 hours) was considerable longer than the cooking and stilling operations time period (about 1 hour).

From wherever the cooling took place (in this example in a separate cooling tank) the PLC (C1) system will then look at the next available fermentation tank (A3). Once the PLC has chosen a tank, the system will verify the tank is empty similar to the method described in the cooker tank empty by observing the presence of lack of material surrounding the ferment low liquid level sensor (A21) within the selected fermentation tank. If the tank is empty, the PLC system will activate through the distributed I/O (B1) the fill solenoid valve (A22) connected to such tank. The cooling tank empty solenoid valve (A23) the cooling tank empty pump (A24) and then pump the material from the cooling tank into the selected fermentation tank. The entire time this material is pumping, the system will optionally duplicate the material flowing verification methods as described above utilized in emptying the cooking tank into the cooling tank to verify that the material is indeed emptying the cooling tank and flowing into the fermentation tank.

Once the material has been pumped from the cooling tank into the fermentation tank, the system may optionally clean the line by purging it with some water similar to that described as an optional clean-out method described above to pump material from the cooking tank. To prevent bacteria from growing in the slurry, the flow of the material from the cooking tank is passed through a microwave or other bacteria killing device (A73). Again, the micro waves will have killed the harmful bacteria contained within the flowing slurry. Yet another method is to cycle a flow of antibiotic through the lines. The goal by the selected means is to kill the harmful bacteria from disturbing the fermentation process.

Once the material is all in the fermentation tank, the cooling tank is made available for the next batch from the cooker and the fermentation process is able to begin within the fermentation tank.

The PLC controller will observe the temperature read from the ferment temp probe (A27) and will activate the ferment cooling solenoid (A28) by sending the activation signal through the distributed I/O (B1) as required to activate the solenoid valve and allow the valve to open and allow cool water to flow through the valve and into the heat exchanger cooling tubes located within the cooling tank. The PLC system will allow this cooling to take place as needed by comparing the retrieved fermentation cooling temperature parameter with the temperature observed from the ferment temperature probe (A27) and continuing cooling the mixture with the cooling water in the cooling solenoids until the desired temperature as retrieved from the batch parameters is achieved. All the while this cooling is taking place, the system will very aggressively agitate the mixture by activating the agitator motor contactors (B9) and turning the agitators. For this invention, (although not a specified requirement) the rotational speed was approximately 300 rpm. This initial agitation and cooling will continue for a time period that was part of the ethanol batch parameters retrieved and compared with the actual cooling time as determined by the PLC. Once the initial cool down of the material has occurred, the PLC system will then enter a longer fermenting time interval. This interval may be of any length but will typically be between 33 and 44 hours. During this fermentation time period, the PLC software will continue to observe the fermentation temperature probe (A27) located in the fermentation tank and attempt to activate the ferment cooling solenoid (A28) as needed to keep the temperature below the fermentation cooling temperature level as defined by the retrieved batch parameters. The fermentation process going on in the material will be creating heat and thus the system needs to periodically cool and agitate the material. The PLC system will also contain as a batch parameter a minimum agitation time interval. This will ensure that the PLC operates the desired fermentation agitator motor (A29) and connected agitator (A30) for a minimum number of seconds per hour. In the example, this was 10 minutes per hour.

While the PLC is cycling agitators on and off about the plant, the system will also observe the total number of agitators operating at any given time and compare this to a stored parameter containing the total number of agitators that may operate in the plant at any one time. This is done because without such a limit, the entire plant may operate too many motors at once and overload the maximum electrical supply available for the plant. If too many agitators need to run at the same time, the system will shut off some of the fermentation tank agitators and operate others, all the while trying to operate the ferment tank actuators as needed for the minimal time period per hour. As the system typically will have 12 fermentation tanks per one cooker, it is the maximum number of ferment tank agitators running at any given time period that is limited for the plant and the cooking, cooling and still agitators are allowed to operate unrestricted.

Once the fermentation time interval has been achieved, all the while at the specified temperatures, the system is then ready to transfer the material to the still stage of the process.

Still Process

Similar to the filling of other tanks, once a tank is fermented, the PLC system will look and identify a next available still. Fermentation completion can be either controlled by allowing for a fermentation time, or by optionally adding equipment to monitor status of fermentation such as a bricks meter, gas meter, or cell growth monitoring device. Either of these means would then inform the PLC that the fermentation process was complete and the material was ready to be transported to the next available still.

The PLC system will then optionally verify the still is empty by observing the low liquid level sensor (A31) in the still tank. If the tank is empty, the PLC system will then activate the selected still fill solenoid valve (A32) and the selected to empty ferment tank empty solenoid (A33) and the ferment tank empty pump (A34).

The material will then be pumped from the selected ferment tank (A3), through the ferment tank empty solenoid valve (A33) through the pipe and into the selected still tank (A4).

The method of opening valves, pumping, verifying pumping is occurring etc. is similar to the method previously described in pumping and verifying material flow from one tank to another.

Once or while the still material is in the still, the still will begin heating up by the PLC activating the still heating device (A35). Such heating device may either be a burner operated by natural gas, methane gas, propane gas or other fuels—or by utilizing a micro wave type heating device.

The PLC will observe the temp on still temp probe (A36) and attempt to continue to activate the heating device through the distribute I/O network node (B10) raising the temperature until the desired temperature has been achieved. In this system—such temp was approximately 163 degrees F. At this temperature, the ethanol alcohol will begin to convert into a vapor. This vapor will then flow up through the still chamber (A37). This chamber can be manufactured in numerous ways. The type as included in the invention utilized a chamber with different segments with each segment containing cooling cools (A38) that are connected to a cooling cool solenoid valve (A39). There are multiple such identical segments with 4 segments used in our current system. Between each of the cooling segments, there is located a still segment temperature probe (A40). The desired still segment temperature for each of the gaps between the segments is stored as one of the retrieved batch parameters. The PLC system will observe the temperature of the temperature probe for each segment and will compare it to the defined desired segment temperature as defined as part of the batch parameters. If the temperature probe becomes too high, the PLC system will activate the still segment cooling solenoid valve (A39) and allow cool water to circulate through the coils to cool down the segment. Each segment will have its own cooling coils, cooling solenoid valve, and defined segment temperature. The segments are cooled at different temperatures to allow for better fracturing of the alcohol from the vapor. At the top of the tank, it is highly recommended (but optional) to locate a pressure relief valve (A41) should for any reason something plug and the vapor not be allowed to escape and be collected. This will help prevent a possible explosion. This relief should be vented to a common collection tank.

The cooled ethanol vapors eventually pass up through and down the still chamber (A37) As the vapors are cooled, they convert to a liquid and are drained through capture basin (A42) This liquid then passed optionally into a gooseneck (A43) which forces a full flow of liquid through liquid meter (A44) and then through inline continuous monitoring ethanol proof meter (A45) The liquid meter (A44) will volumetrically monitor the amount of ethanol produced and transmit this amount through the distributed I/O network (B10) to the PLC to record the amount of ethanol produced from the batch. The continuous proof meter (A45) measures the proof of the ethanol and transmits this via a 4-20 ma (or other communication means) to the distributed I/O network (B10) back to the PLC (C1). This then allows the PLC to record and store in memory on the hard drive of primary server computer (C2) the actual proof of the ethanol produced. If the proof does not fall above the defined and retrieved batch parameter requirements, an operator alarm is displayed on the display console monitor screen (C3). This then would allow the operator to distribute the low proof ethanol to a different container for further distilling and proof verification.

While the removing of the ethanol is taking place in the still, the system may optionally activate a sonic device (A46) directed into the still chamber. This sonic device (A46) will also aid in the fracturing and removal of still additional molecules of ethanol.

Once the desired slurry temperature as recorded by still temperature probe (A36) is achieved and is maintained for the desired minimum time interval as defined by the retrieved batch parameters, the PLC system will then observe flow/no flow through the volume meter (A44). This measuring of the amount of ethanol produced can be measured in a variety of ways and is not dependent on the volumetric method. Another such method would be to pass the liquid ethanol into a container that is weighed. Either way, the ethanol is allowed to flow into an ethanol collection tank of some means.

Separating Process

Once all of the desired ethanol is removed, the PLC system will remove the remaining slurry from the still tank by activating still empty solenoid (A47), turning on still empty pump (A48) and pumping the remaining material to the desired location. This may be directly to a container as a byproduct, or optionally to a separator. The system will continue to pump the material until the PLC observes that material is no longer present at the still low level sensor (A31). It will then continue pumping for a predefined time period as was utilized in the aforementioned tank emptying process. The optional separator process is described in further detail below.

If utilized, the PLC system will select separator (A49) by activating the separator fill solenoid valve (A50) and turning on the still empty pump (A48). The slurry is then pumped into the separator (A49). The heavy grain material is removed by the PLC activating the separator motor contactor contained in the closest control panel via the distributed I/O network which activates the desired separator motor (A51) to rotate the screen on the separator. This rotating screen collects material on the surface of the drum rotating screen (A52) which then collects solid material on its surface. Air is sucked through this screen by activating the vacuum blower (A53). This then sucks air through the material and the screen acting to somewhat dry and collect the material. The solid material is then scraped off with the separator scraper (A54) and dropped into a solids conveyor (A55) where it is conveyed to a storage location or to a pellet mill. This nutrient rich by product material is then available to be used as feed for animals or other uses.

The remaining liquid is pumped to a beer holding tank by the PLC system activating the separator empty solenoid valve (A56) and separator empty pump (A57) This material is then pumped into the beer holding tank until the PLC observes the level falling below separator low level sensor (A58).

The PLC software system will allow all of the various phases of the process to operate simultaneously with the cooker tank cooking, the cooling tank cooling, each of the ferment tanks fermenting, the still taking off the ethanol and the separator separating solids and liquids from the byproduct—all occurring simultaneously. All of this data is fed back into the master control PLC and the to various PC command screens (C2) located about the plant. Similarly, the process as defined was for just one ethanol producing unit contained within the plant. The control system as defined can be duplicated many times with many simultaneous execution of the software process and on multiple PLCs all connected to one server. This allows for a very large amount of ethanol to be produced. As an example, a system of 64 duplicate simultaneous systems will produce about 60 million gallons of ethanol per year at a conversion rate in excess of 3 gallons per bushel of corn.

The PLCS are also able to run a SCADA type automation display on the control monitor (C3) that allows the entire plant to be operated by one or many users. The system will also capture all of the data available for storing and tracking the production of ethanol.

The SCADA display will display the various sensors and equipment operation throughout the plant and provide for automatic or manual control of all devices.

The master control SCADA will also record and store the historical parameters of all ethanol produced and utilized batch parameters for every batch produced. This then allows considerable data to be captured for data analysis and increased efficiency improvements.

An example of such an implementation may include the system preparing ethanol from many different types of grains of different genetics. Since each batch is typically very small (about 97 bushels of corn or other material) very little of any type of sample grain is needed to provide data on the conversion capabilities.

The end result of the entire system is an automatic labor efficient method of making large or small volumes of ethanol in a very efficient manner, with very few released pollutants, a very high feed content byproduct due to much of the fat still remaining in the byproduct, and much higher yield of ethanol.

Finally, because the system is built from many small tanks, virtually any non utilized empty building can be converted into an ethanol production facility with a minimum of building facility conversion required.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An automated batch ethanol production system comprising:
    a primary logic controller including stored parameters for producing ethanol, the logic controller being electronically coupled to a plurality of input/output points located throughout the system;
    a cooker tank disposed to receive quantities of water, corn mash, enzyme, heat and agitation, the quantities being determined by the stored parameters;
    a microwave device used to raise a temperature of contents of the cooker tank to a predetermined cooking temperature and to increase yields of ethanol;
    a plurality of fermentation tanks each being disposed to receive quantities of contents from the cooker tank, fermentation activation materials, cooling and agitation, the quantities being determined by the stored parameters; and
    a still tank disposed to receive quantities of contents from the fermentation tanks, heating and cooling, the quantities being determined by the stored parameters.

2. The system of claim 1 further including:
    a cooler tank, independent of the cooker tank and the still tank, disposed to receive quantities of the contents from the cooker tank and cooling, the quantities being determined by the stored parameters.

3. The system of claim 1 further including:
    a separator disposed to receive quantities of a slurry from the still tank and vacuum, the quantities being determined by the stored parameters, said separator to separate liquid components from solid components of the slurry.

4. The system of claim 2 further including:
    a separator disposed to receive quantities of a slurry from the still tank and vacuum, the quantities being determined by the stored parameters, said separator to separate liquid components from solid components of the slurry.

5. The system of claim 1 wherein the cooker tank, the fermentation tanks, and the still tank are in a system of small tanks with distributed intelligent remote input/output points connected together in a network with some of the logic path occurring in the remote input/output and some of the logic path occurring in the primary logic controller to reduce the level of activity and enable the functioning of a multiple small tank system with a large volume of input/output control points.

6. An automated batch ethanol production method, comprising:
    providing a primary logic controller including stored parameters for producing ethanol, the logic controller being electronically coupled to a plurality of input/output points located throughout the system;
    providing a cooker tank disposed to receive quantities of water, corn mash, enzyme, heat and agitation, the quantities being determined by the stored parameters;
    raising a temperature of contents of the cooker tank to a predetermined cooking temperature using a microwave device disposed to treat cooker tank contents for heat and to increase yields;
    providing a plurality of fermentation tanks each being disposed to receive quantities of contents from the cooker tank, fermentation activation materials, cooling and agitation, the quantities being determined by the stored parameters;
    providing a still tank disposed to receive quantities of contents from the fermentation tanks, heating and cooling, the quantities being determined by the stored parameters; and
    producing ethanol in an automated batch process using the primary logic controller, microwave device, cooker tank, plurality of fermentation tanks and still tank.

7. The method of claim 6 further including:
    providing a cooler tank disposed to receive quantities of the contents from the cooker tank and cooling, the quantities being determined by the stored parameters, said cooler tank being independent of the cooker tank and the still tank.

8. The method of claim 6 further including:
    providing a separator disposed to receive quantities of a slurry from the still tank and vacuum, the quantities being determined by the stored parameters; and
    separating solid components from liquid components of the slurry by the separator.

9. The method of claim 7 further including:
    providing a separator disposed to receive quantities of a slurry from the still tank and vacuum, the quantities being determined by the stored parameters; and separating solid components from liquid components of the slurry by the separator.

10. The method of claim 6 wherein the cooker tank, the fermentation tanks, and the still tank are in a system of small tanks with distributed intelligent remote input/output points connected together in a network with some of the logic path occurring in the remote input/output and some of the logic path occurring in the primary logic controller to reduce the level of activity and enable the functioning of a multiple small tank system with a large volume of input/output control points.

11. The system of claim 1, further including a sonic device directed into the still tank to enhance the removal of ethanol.

12. An automated batch ethanol production system comprising:
   a primary logic controller including stored parameters for producing ethanol, the logic controller being electronically coupled to a plurality of input/output points located throughout the system;
   a cooker tank disposed to receive quantities of water, corn mash, enzyme, heat and agitation, the quantities being determined by the stored parameters;
   a microwave heating device used to raise a temperature of contents of the cooker tank to a predetermined, cooker temperature as well as to increase yields of ethanol;
   a bacteria killing device disposed to treat contents from the cooker tank;
   a plurality of fermentation tanks each being disposed to receive quantities of contents from the cooker tank, fermentation activation materials, cooling and agitation, the quantities being determined by the stored parameters;
   a still tank disposed to receive quantities of contents from the fermentation tanks, heating and cooling, the quantities being determined by the stored parameters; and
   a sonic device directed into the still tank to enhance the removal of ethanol.

13. The system of claim 12 further including:
   a cooler tank disposed to receive quantities of the contents from the cooker tank and cooling, the quantities being determined by the stored parameters.

14. The system of claim 12 further including:
   a separator disposed to receive quantities of a slurry from the still tank and vacuum, the quantities being determined by the stored parameters.

15. The system of claim 12 wherein the bacteria killing device is a microwave device.

16. The method of claim 6 further including providing a sonic device directed into the still tank to enhance the removal of ethanol.

17. The method of claim 6 additionally comprising maintaining the contents of the cooker tank near the predetermined cooking temperature using the microwave device.

* * * * *